United States Patent [19]
Yamazaki et al.

[11] Patent Number: 5,789,419
[45] Date of Patent: Aug. 4, 1998

[54] 4-QUINOLINONE DERIVATIVE OR SALT THEREOF

[75] Inventors: Kazuo Yamazaki, Sawara; Shigeru Adegawa, Narita; Yoichiro Ogawa, Chiba; Hideaki Matsuda, Abiko; Tadayuki Kuraishi, Narashino, all of Japan

[73] Assignee: SS Pharmaceutical Co., Ltd., Tokyo, Japan

[21] Appl. No.: 750,146

[22] PCT Filed: Jun. 6, 1995

[86] PCT No.: PCT/JP95/01118

§ 371 Date: Dec. 9, 1996

§ 102(e) Date: Dec. 9, 1996

[87] PCT Pub. No.: WO95/33726

PCT Pub. Date: Dec. 14, 1995

[30] Foreign Application Priority Data

Jun. 9, 1994 [JP] Japan ................... 6-127573

[51] Int. Cl.$^6$ ............... A61K 3/47; C07D 215/58
[52] U.S. Cl. ............... 514/312; 546/156; 546/159
[58] Field of Search ............... 514/312; 516/153, 516/159

[56] References Cited

U.S. PATENT DOCUMENTS 5,175,151  12/1992  Afonso ................... 514/63

FOREIGN PATENT DOCUMENTS

| | | |
|---|---|---|
| 0 168 619 | 1/1986 | European Pat. Off. . |
| 0 413 438 | 2/1991 | European Pat. Off. . |
| 0 432 893 | 6/1991 | European Pat. Off. . |
| 0 488 616 | 6/1992 | European Pat. Off. . |
| WO 92/22293 | 12/1992 | WIPO . |

OTHER PUBLICATIONS

David W. Robertson et al., Journal of Medicinal Chemistry, "Potassium Channel Modulators: Scientific Applications and Therapeutic Promise," vol. 33, No. 6, Jun. 1990, pp. 1529–1541.

Gillian Edwards et al., "Structur–Activity Relationships of K+ Channel Openers," vol. 11, No. 10, Oct. 1990, pp. 417–422.

Valerie A. Ashwood et al., "Synthesis and Antihypertensive Activity of Pyran Oxygen and Amide Nitrogen Replacement Analoges of the Potassium Channel Activator Cromakalim," Journal of Medicinal Chemistry, vol. 34, No. 11, Nov. 1991, pp. 3261–3267.

Susan D. Longman et al., "Potassium Channel Activator Drugs: Mechanism of Action, Pharmacological Properties, and Therapeutic Potential," Medicinal Research Reviews, vol. 12, No. 2, Mar. 1, 1992, pp. 73–148.

Karnail S. Atwal, "Modulation of Potassium Channels by Organic Molecules," Medicinal Research Reviews, vol. 12, No. 6, Nov. 1992, pp. 569–591.

Primary Examiner—Alan L. Rotman
Assistant Examiner—D. Margaret M. Mach
Attorney, Agent, or Firm—Oblon, Spivak, McClelland, Maier & Neustadt, P.C.

[57] ABSTRACT

This invention relates to a 4-quinolinone derivative represented by the following general formula (1):

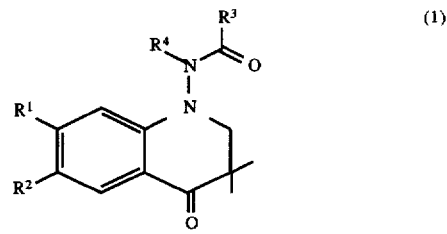

wherein $R^1$ and $R^2$ mean individually H, halogen, cyano, or lower alkyl, lower alkylsulfonyl, lower alkylsulfinyl, lower alkylthio or lower alkoxy which may be substituted by halogen, or phenylsulfonyl, phenylsulfinyl or phenylthio which may have a substituent; and $R^3$ and $R^4$ denote individually H, lower alkyl or cycloalkyl which may be substituted by halogen, or pyridyl, furanyl or phenyl which may have a substituent, or $R^3$ and $R^4$ may form a 4-, 5- or 6-membered heterocyclic ring, or a salt thereof, and an intermediate useful for the preparation thereof, and besides a medicinal composition comprising this compound as an active ingredient. The compound (1) or the salt thereof has an excellent potassium channel-activating effect and is useful as, for example, a prophylactic and therapeutic agent for diseases of circulatory and bronchial systems.

9 Claims, No Drawings

4-QUINOLINONE DERIVATIVE OR SALT THEREOF

This application is a 371 of PCT/JP95/01118, filed on 6 Jun. 1995.

1. Technical Field

The present invention relates to a 4-quinolinone derivative or a salt thereof, which is useful as a medicine, in particular, as a prophylactic and therapeutic agent for diseases of circulatory and bronchial systems, an N-amino-4-quinolinone derivative or a salt thereof, which is an intermediate useful for the preparation thereof, and a medicinal composition comprising the 4-quinolinone derivative as an active ingredient.

2. Background Art

Drugs having a smooth muscle-activating effect, for example, direct smooth muscle relaxants, calcium antagonists, β-blockers, α-blockers, etc., have heretofore been widely used as prophylactic and therapeutic agents for diseases of circulatory system, such as ischemic heart diseases such as angina pectoris and myocardial infarction, and hypertension, bronchial asthma, and the like. However, all of these drugs involve such problems that their pharmacological effects are insufficient, and they cause many side effects. There is hence a demand for development of a therapeutic agent which is more effective and safer.

Therefore, smooth muscle relaxants having a new mechanism called the "potassium channel-activating action" on smooth muscle cells have been developed in recent years and attracted considerable attention as therapeutic agents for diseases of circulatory and bronchial systems. As compounds having a potassium channel-activating effect, which are active ingredients in such remedies, there have been known Cromakalim [(±)-trans-6-cyano-2,2-dimethyl-4-(2-oxopyrrolidin-1-yl)-3,4-dihydro-2H-1-benzopyran-3-ol] and the like.

However, the conventional compounds having a potassium channel-activating effect cannot be said to be fully satisfactory medicines in view of both effectiveness and safety. It is therefore an object of the present invention to provide a compound having a potassium channel-activating effect, which is excellent in both effectiveness and safety.

DISCLOSURE OF THE INVENTION

Thus, the present inventors have synthesized a great number of compounds and screened such compounds by using a potassium channel-activating effect as an index. As a result, it has been found that a 4-quinolinone derivative or a salt thereof, which has a specific structure, has a strong potassium channel-activating effect and is also useful as a medicine for treating circulatory diseases and bronchial diseases, thus leading to completion of the present invention.

According to the present invention, there is thus provided a 4-quinolinone derivative represented by the following general formula (1):

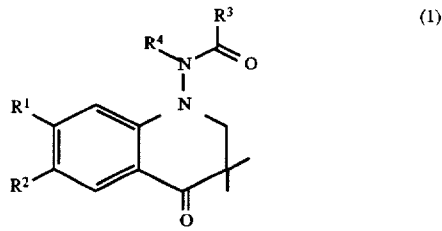

wherein $R^1$ and $R^2$ may be the same or different from each other and mean individually a hydrogen atom; a halogen atom; a cyano group; a lower alkyl, lower alkylsulfonyl, lower alkylsulfinyl, lower alkylthio or lower alkoxy group which may be substituted by halogen atom; or a phenylsulfonyl, phenylsulfinyl or phenylthio group which may have a substituent; and $R^3$ and $R^4$ may be the same or different from each other and denote individually a hydrogen atom; a lower alkyl or cycloalkyl group which may be substituted by halogen atom; or a pyridyl, furanyl or phenyl group which may have a substituent, or $R^3$ and $R^4$ may form a 4-, 5- or 6-membered heterocyclic ring, which may be substituted by a lower alkyl group, together with the adjacent carbon atom and nitrogen atom, or a salt thereof.

According to the present invention, there is also provided a medicinal composition comprising the 4-quinolinone derivative or the salt thereof and a pharmaceutically acceptable carrier.

According to the present invention, there is further provided use of the 4-quinolinone derivative or the salt thereof for a medicine.

According to the present invention, there is still further provided an N-amino-4-quinolinone derivative represented by the following general formula (2):

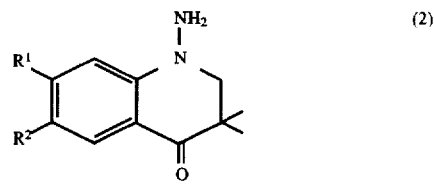

wherein $R^1$ and $R^2$ may be the same or different from each other and mean individually a hydrogen atom; a halogen atom; a cyano group; a lower alkyl, lower alkylsulfonyl, lower alkylsulfinyl, lower alkylthio or lower alkoxy group which may be substituted by halogen atom; or a phenylsulfonyl, phenylsulfinyl or phenylthio group which may have a substituent, or a salt thereof, said derivative or salt being an intermediate useful for the preparation of the 4-quinolinone derivative represented by the general formula (1) or the salt thereof.

BEST MODE FOR CARRYING OUT THE INVENTION

The meanings of $R^1$, $R^2$, $R^3$ and $R^4$ in the general formulae (1) and (2) are as described above, and more specifically are as follows:

Examples of the halogen atom may include fluorine, chlorine, bromine and iodine atoms.

Examples of the lower alkyl group may include linear or branched alkyl groups having 1–6 carbon atoms, such as methyl, ethyl, propyl, isopropyl, butyl and isobutyl groups.

Examples of the lower alkoxy group may include linear or branched alkoxy groups having 1–6 carbon atoms, such as methoxy, ethoxy, propoxy and isopropoxy groups.

Examples of the cycloalkyl group may include cycloalkyl groups having 3–6 carbon atoms, such as cyclopropyl, cyclobutyl, cyclopentyl and cyclohexyl groups.

Examples of the lower alkylsulfonyl group may include linear or branched alkylsulfonyl groups having 1–6 carbon atoms, such as methylsulfonyl, ethylsulfonyl, propylsulfonyl and isopropylsulfonyl groups.

Examples of the lower alkylsulfinyl group may include linear or branched alkylsulfinyl groups having 1–6 carbon atoms, such as methylsulfinyl, ethylsulfinyl, propylsulfinyl and isopropylsulfinyl groups.

Examples of the lower alkylthio group may include linear or branched alkylthio groups having 1–6 carbon atoms, such as methylthio, ethylthio, propylthio and isopropylthio groups.

These lower alkyl, lower alkylsulfonyl, lower alkylsulfinyl, lower alkylthio, lower alkoxy and cycloalkyl groups may be substituted by 1–3 halogen atoms. Specific examples of the substituted groups include groups with 1–3 halogen atoms substituted on the respective groups specifically mentioned above.

In the cases where the phenylsulfonyl, phenylsulfinyl or phenylthio group has a substituent and where the pyridyl, furanyl or phenyl group has a substituent, examples of the substituents may include halogen atoms, a hydroxyl group, alkoxy groups having 1–6 carbon atoms, aryloxy groups (for example, a phenyloxy group), aralkyloxy groups (for example, phenylalkyloxy groups), a nitroxy group, an amino group, a cyano group, a nitro group, alkylamino groups having 1–6 carbon atoms, dialkylamino groups having 2–12 carbon atoms, cyclic amino groups (for example, pyrrolidinyl and piperidinyl groups), aryl groups (for example, a phenyl group), an aminosulfonyl group and alkyl groups having 1–6 carbon atoms.

Examples of the 4-, 5- or 6-membered heterocyclic ring which is formed by $R^3$ and $R^4$ together with the adjacent carbon atom and nitrogen atom may include 2-oxoazetidinyl, 2-oxopyrrolidinyl and 2-oxopiperidinyl groups. These heterocyclic rings may be substituted by 1–3 linear or branched alkyl groups having 1–6 carbon atoms.

As salts of the 4-quinolinone derivative, may be mentioned pharmaceutically acceptable salts, for example, inorganic acid salts such as the hydrochloride, nitrate, sulfate and hydrobromate; and organic acid salts such as the lactate, malonate, fumarate, maleate, succinate, citrate and acetate.

The 4-quinolinone derivative (1) and N-amino-4-quinolinone derivative (2) according to the present invention include their hydrates and solvates, and further their optically active substances if optical isomers are present.

The 4-quinolinone derivative (1) or the salt thereof according to the present invention can be prepared, for example, in accordance with the following reaction scheme:

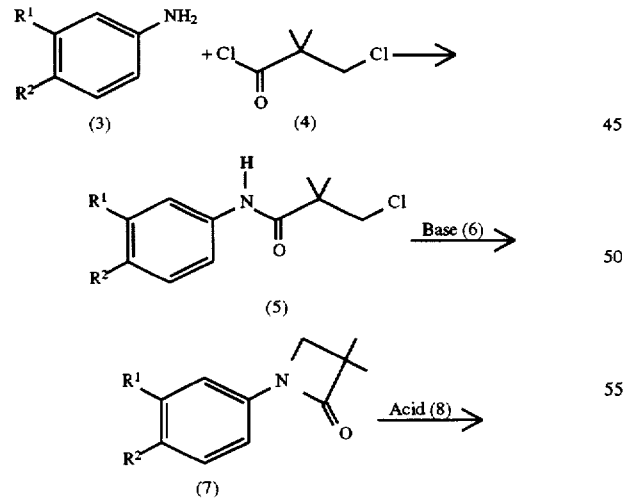

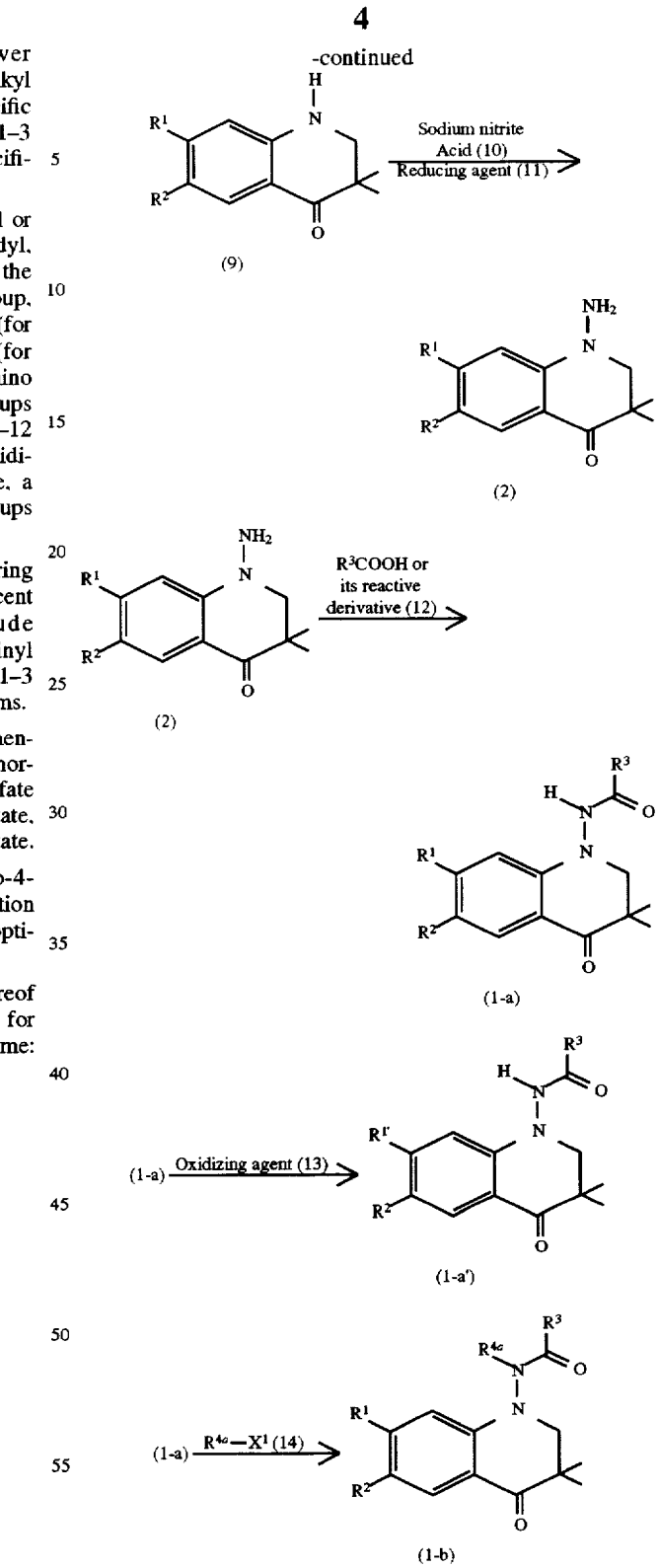

-continued

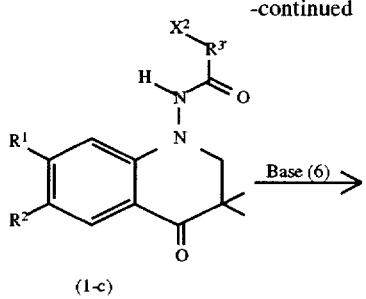

(1-c)

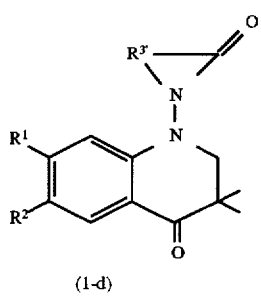

(1-d)

wherein $R^{1'}$ means a lower alkylsulfonyl or lower alkylsulfinyl group which may be substituted by halogen atom, $R^{4a}$ denotes a lower alkyl group, $R^{3'}$ is an alkylene group having 2–6 carbon atoms, which may be branched, $X^1$ and $X^2$ stand individually for a halogen atom, and $R^1$, $R^2$ and $R^3$ have the same meaning as defined above.

Namely, aniline or its derivative (3) is reacted with 3-chloro-2,2-dimethylpropionyl chloride (4) to prepare a compound (5). The compound (5) is cyclized, thereby preparing a compound (7). This compound is treated with an acid, thereby preparing a compound (9) which is then treated with an acid and sodium nitrite to prepare a nitroso compound. The nitroso compound is then reduced with a reducing agent, thereby preparing an N-amino-4-quinolinone derivative (2).

The N-amino-4-quinolinone or its derivative (2) is then reacted with a carboxylic acid or its reactive derivative (12), thereby preparing a compound (1-a). The compound (1-a) is treated with a suitable oxidizing agent (13), thereby preparing a compound (1-a'). Further, the compound (1-a) is reacted with a lower alkyl halide (14) which may have a substituent, thereby preparing a compound (1-b). Besides, a compound (1-c) is treated with a suitable base (6) to cyclize, thereby obtaining a compound (1-d).

The individual reaction steps of the above reaction scheme will hereinafter be described in detail.

First of all, the reaction of aniline or its derivative (3) with 3-chloro-2,2-dimethylpropionyl chloride (4) is conducted, for example, with stirring at 0° C. to room temperature for 0.1 to several hours in a solvent.

Examples of the solvent may include methylene chloride, chloroform, diethyl ether, tetrahydrofuran, dioxane, dimethylformamide, pyridine, benzene, toluene, xylene, ethyl acetate and acetonitrile. The reaction is preferably conducted in the presence of a base. Examples of the base may include organic bases such as triethylamine, pyridine and dimethylaniline, and inorganic bases such as sodium hydrogencarbonate, potassium carbonate, sodium carbonate, potassium hydroxide and sodium hydroxide.

The cyclization reaction of the resultant compound (5) is performed by treating the compound (5) with the base (6). This reaction is conducted, for example, with stirring at 0° C. to room temperature for 0.1–24 hours in a solvent.

Examples of the solvent may include methanol, ethanol, diethyl ether, tetrahydrofuran, dioxane, benzene, toluene, xylene and dimethylformamide. Besides, examples of the base may include sodium hydride, sodium alcoholates, sodium amide, sodium hydroxide and potassium hydroxide.

The reaction in which the resultant compound (7) is treated with the acid (8) to obtain the compound (9) is preferably performed with stirring at room temperature to 100° C. for 0.5–24 hours.

Examples of the acid may include sulfuric acid, polyphosphoric acid, trifluoromethanesulfonic acid and trifluoroacetic acid.

The reaction in which the nitroso compound is obtained from the compound (9) is conducted, for example, with stirring at 0° C. to room temperature for 1–100 hours in the presence of an acid in a solvent. Examples of the solvent may include lower alcohols miscible with water in any optional proportion, such as methanol, ethanol and propanol, dioxane, and tetrahydrofuran. Examples of the acid nay include inorganic acids such as hydrochloric acid, sulfuric acid and nitric acid, and organic acids such as acetic acid.

The reducing reaction of the resultant nitroso compound is performed with stirring at 0° C. to room temperature for 0.1 to several hours in the presence of an acid and a reducing metal such as zinc or tin in a solvent. As the solvent, may be mentioned one or more of water, methanol, ethanol, propanol, dioxane and tetrahydrofuran.

The reaction of the resultant N-amino-4-quinolinone derivative (2) with the carboxylic acid or its reactive derivative (12) is preferably conducted at 0° C. to a reflux temperature for 1–24 hours.

The meanings of $R^1$ and $R^2$ in the N-amino-4-quinolinone (2) are as defined above and more specifically, are the same as those in the 4-quinolinone derivative (1). Besides, examples of the reactive derivative of the carboxylic acid (12) may include esters such as a methyl ester and an ethyl ester, acid halides such as an acid chloride, an acid anhydride, and an acid anhydride mixed with a carbonic acid ester or the like.

When the carboxylic acid (12) is reacted in the form of a free acid, it may be directly reacted. However, it is preferably reacted in the presence of a condensation agent such as dicyclohexylcarbodiimide. There is no need to use a solvent in the reaction. However, methylene chloride, chloroform, diethyl ether, tetrahydrofuran, dioxane, dimethylformamide, pyridine, benzene, toluene, xylene, ethyl acetate, acetonitrile or the like may also be used. The reaction is preferably conducted in the presence of a base. Examples of the base may include organic bases such as triethylamine, pyridine and dimethylaniline, and inorganic bases such as sodium hydrogencarbonate, potassium carbonate, sodium carbonate, potassium hydroxide and sodium hydroxide.

The reaction in which the compound (1-a') is obtained from the compound (1-a) is preformed, for example, with stirring at 0° C. to a reflux temperature for 0.1 to several hours in a solvent.

Examples of the oxidizing agent (13) may include hydrogen peroxide, peracids such as peracetic acid, perbenzoic acid and m-chloroperbenzoic acid, sodium metaperiodate, hydroperoxides, ozone, selenium dioxide, chromic acid, dinitrogen tetraoxide, acyl nitrate, iodine, bromine, N-bromosuccinimide, iodosylbenzene, sulfuryl chloride and water-containing silica gel, and t-butyl hypochlorite. Examples of the solvent may include chloroform, methylene chloride, benzene, toluene, xylene, acetic acid, water and alcohol.

The reaction of the compound (1-a) with the lower alkyl halide (14) which may have a substituent is conducted, for example, with stirring at 0° C. to room temperature for 0.1–24 hours in the presence of a base in a solvent.

Examples of the solvent may include diethyl ether, tetrahydrofuran, dioxane, benzene, toluene, xylene and dimethylformamide. Besides, examples of the base may include sodium hydride, sodium alcoholates and sodium amide.

The reaction in which the compound (1-d) is obtained from the compound (1-c) is performed, for example, with stirring at 0° C. to room temperature for 0.1–24 hours in a solvent.

Examples of the solvent may include diethyl ether, tetrahydrofuran, dioxane, benzene, toluene, xylene and dimethylformamide. Besides, examples of the base may include sodium hydride, sodium alcoholates and sodium amide.

As a method for isolating the intended compound in each of the above reactions, methods known per se in the art, such as washing, extraction, recrystallization and column chromatography on silica gel may be suitably used either singly or in any combination thereof.

The 4-quinolinone derivative (1) according to the present invention has an effect of inhibiting smooth muscle contraction on the basis of its potassium channel-activating effect as shown in Test Example, which will be described subsequently, and is hence useful as a prophylactic and therapeutic agent for various diseases of circulatory and bronchial systems, which are caused by the contraction of a smooth muscle. Here, examples of the circulatory diseases include ischemic heart diseases such as angina pectoris and myocardial infarction, and hypertension, and examples of the bronchial diseases include bronchial asthma.

When the 4-quinolinone derivative (1) or the salt thereof is used as such a medicine, it can be used by itself or in the form of a medicinal composition with other pharmaceutically acceptable carriers for medicines.

This composition can be orally or parenterally administered to the human and formulated into desired preparation forms such as tablets, granules, powders, capsules, suspensions, solutions, syrups, elixirs, oil-based and water-based suspensions, injections, suppositories, ointments, gels, creams and lotions.

When the composition is provided as a solid preparation, it can be prepared by using excipients such as starch, lactose, carboxymethylcellulose, sorbit and precipitated calcium carbonate, binders such as syrup, gum arabic, tragacanth gum, gelatin and methylcellulose, disintegrators such as alginic acid and corn starch, lubricants such as magnesium stearate and talc, colorants, taste and smell corrigents such as menthol, sugar-coatings such as saccharose. When the composition is provided as an injection preparation, stabilizers, antiseptics, emulsifiers and the like may be incorporated into the preparation. The composition may be provided as powder for injection, which is dissolved into an injection at the time it will be used. Preparation Examples will hereinafter be mentioned.

The dose of this medicine varies according to the weight, age, sex of a patient to be dosed, an administration method, the physical condition and diseased condition of the patient, and the like. However, it is suitably dosed in a proportion of 0.05–5 mg/kg of weight/day in terms of the 4-quinolinone derivative (1) or the salt thereof for a man in the case of oral administration. In the case of parenteral administration, it is suitably dosed in a proportion of 0.01–1 mg/kg of weight/day. This medicine may be dosed at once or in several portions a day.

EXAMPLES

The present invention will hereinafter be described in more detail by the following examples. However, the present invention is not limited by these examples.

Referential Example 1

N-[3-(Trifluoromethyl)phenyl]-2-chloromethyl-2-methyl-propionamide:

Added to a solution of 16.1 g of 3-(trifluoromethyl)-aniline in methylene chloride were 16.7 ml of triethylamine, and 14.2 ml of 3-chloro-2,2-dimethylpropanoyl chloride were added dropwise under chilling with ice water. After stirring the mixture at room temperature for 1 hour, the resulting liquid reaction mixture was washed once each with water and saturated saline and dried on magnesium sulfate. Methylene chloride was distilled off, and the residue was purified by column chromatography on silica gel to obtain 28 g (yield: 100%) of the title compound.

$^1$H-NMR (CDCl$_3$, δ ppm): 7.30–7.92(5H,m), 3.72(2H,s), 1.46(6H,s).

Referential Example 2

N-[3-(Trifluoromethyl)phenyl]-3,3-dimethylazetidin-2-one:

Dissolved in dimethylformamide were 1.4 g of N-[3-(trifluoromethyl) phenyl]-2-chloromethyl-2-methylpropionamide, and 0.24 g of sodium hydride were added with stirring at 5° C. After stirring the mixture at room temperature for 15 hours, it was added with ice water and extracted with diethyl ether. The extract was dried over magnesium sulfate. Diethyl ether was distilled off, and the residue was purified by column chromatography on silica gel to obtain 1.00 g (yield: 82%) of the title compound.

$^1$H-NMR (CDCl$_3$, δ ppm): 7.22–7.70(4H,m), 3.47(2H,s), 1.46(6H,s).

Referential Example 3

2,3-Dihydro-3,3-dimethyl-7-(trifluoromethyl)-4(1H)-quinolinone (Compound No. 1):

Added to 20.16 g of N-[3-(trifluoromethyl)phenyl]-3,3-dimethylazetidin-2-one were 320 g of polyphosphoric acid, and the mixture was stirred at 80°–90° C. for 4 hours. After completion of the reaction, the liquid reaction mixture was poured into ice water and extracted with chloroform. The resultant chloroform layer was washed successively with a saturated aqueous solution of sodium hydrogencarbonate and saturated saline and dried over magnesium sulfate. Chloroform was distilled off, and the residue was purified by column chromatography on silica gel to obtain 7.54 g (yield: 37%) of the title compound as colorless crystals.

m.p.: 121°–122° C.

IR (KBr method, cm$^{-1}$): 3370, 1668.

$^1$H-NMR (CDCl$_3$, δ ppm): 7.95(1H,d,J=8 Hz), 6.86–7.00 (2H,m), 4.69(1H,br.), 3.32(2H,d,J=3 Hz), 1.22(6H,s).

Referential Example 4

Respective compounds (Compound Nos. 2–10) shown in Tables 1–3 were obtained in the same manner as in Referential Examples 1–3.

TABLE 1

| Compd. No. | Structural formula | mp (°C.) | IR(cm⁻¹) | NMR δ ppm(CDCl₃) |
|---|---|---|---|---|
| 1 | CF₃-(phenyl)-NH-(ring)-C(CH₃)₂-C(=O) | 121–122 | 3370<br>1668 | 7.95(1H, d, J=8Hz), 6.86–7.00(2H, m), 4.69(1H, br), 3.32(2H, d, J=3Hz), 1.22(6H, s) |
| 2 | CF₃S-(phenyl)-NH-(ring)-C(CH₃)₂-C(=O) | 133–134 | 3365<br>1655<br>1612 | 7.87(1H, d, J=8Hz), 6.83(2H, m), 4.62(1H, br), 3.29 (2H, d, J=2Hz), 1.18(6H, s) |
| 3 | Br-(phenyl)-NH-(ring)-C(CH₃)₂-C(=O) | 146–147 | 3365<br>1654<br>1607 | 7.72(1H, d, J=8Hz), 6.86(2H, m), 4.50(1H, br), 3.26 (2H, d, J=2Hz), 1.16(6H, s) |
| 4 | CF₃O-(phenyl)-NH-(ring)-C(CH₃)₂-C(=O) | 94–95 | 3348<br>1654<br>1265 | 7.90(1H, d, J=8Hz), 6.42–6.66(2H, m), 4.62(1H, br), 3.28(2H, d, J=3Hz), 1.17(6H, s) |

TABLE 2

| Compd. No. | Structural formula | mp (°C.) | IR(cm⁻¹) | NMR δ ppm(CDCl₃) |
|---|---|---|---|---|
| 5 | MeS-(phenyl)-NH-(ring)-C(CH₃)₂-C(=O) | 103–104 | 3313<br>1630<br>1601 | 7.76(1H, d, J=8Hz), 6.60(1H, dd, J=8.2Hz), 6.43(1H, d, J=2Hz), 4.50(1H, brs), 3.24(2H, d, J=3Hz), 2.44 (3H, s), 1.15(6H, s) |
| 6 | PhS-(phenyl)-NH-(ring)-C(CH₃)₂-C(=O) | 110–111 | 3360<br>1654<br>1594 | 7.74(1H, d, J=8Hz), 7.28–7.60(5H, m), 6.52(1H, dd, J=8.2Hz), 6.32(1H, d, J=2Hz), 4.36(1H, brs), 3.20 (2H, d, J=3Hz), 1.13(6H, s) |
| 7 | Cl,Cl-(phenyl)-NH-(ring)-C(CH₃)₂-C(=O) | 145–147 | 3350<br>1655 | 7.90(1H, s), 6.82(1H, s), 4.64(1H, brs), 3.30, 3.22 (2H, ABq), 1.16(6H, s) |

TABLE 2-continued

| Compd. No. | Structural formula | mp (°C.) | IR(cm⁻¹) | NMR δ ppm(CDCl₃) |
|---|---|---|---|---|
| 8 | NC-[ring]-N(H), C(=O), dimethyl | 135–137 | 2228 1660 1619 1280 | 7.93(1H, d, J=9Hz), 7.00(1H, d, J=1Hz), 6.95(1H, dd, J=9.1Hz), 4.65(1H, br), 3.34, 3.27(2H, ABq), 1.18 (6H, s) |

TABLE 3

| Compd. No. | Structural formula | mp (°C.) | IR(cm⁻¹) | NMR δ ppm(CDCl₃) |
|---|---|---|---|---|
| 9 | PhSO₂-[ring]-N(H), C(=O), dimethyl | 143–144 | 3370 1660 1610 1318 1154 | 7.95(2H, d, J=7.5H, 7.92(1H, d, J=8.5Hz), 7.60(1H, d, J=7.5Hz), 7.52(2H, t, J=7.5Hz), 7.38(1H, d, J= 1.5Hz), 7.13(1H, dd, J=8.5, 1.5Hz), 5.05(1H, brs), 3.28(1H, 1/2ABq), 3.27(1H 1/2ABq), 1.14(6H, s) |
| 10 | MeO-[ring]-N(H), C(=O), dimethyl | 77–79 | 3345 1651 1526 1280 1035 | 7.36(1H, d, J=3Hz), 6.98(1H, dd, J=3.9Hz), 6.62(1H, d, J=9Hz), 4.28(1H, br), 3.76(3H, s), 3.22(2H, s), 1.17(6H, s) |

Example 1

1-Amino-2,3-dihydro-3,3-dimethyl-7-phenylsulfonyl-4 (1H)-quinolinone (Compound No. 19):

Added to a solution of 7.6 g of 2,3-dihydro-3,3-dimethyl-7-phenylsulfonyl-4(1H)-quinolinone in ethanol were 20.8 ml of acetic acid, and an aqueous solution of 25.1 g of sodium nitrite was added with stirring at room temperature. After stirring the resultant mixture at room temperature for 36 hours, the liquid reaction mixture was added with water and extracted with ethyl acetate. After the extract was dried over magnesium sulfate, the solvent was distilled off. The residue was dissolved in ethanol, and 8.3 ml of acetic acid were added to the solution. While stirring the mixture at 0° C., 9.3 g of zinc powder were gradually added. After stirring at room temperature for 4 hours, zinc was removed by filtration. After the filtrate was concentrated, water was added, and the liquid reaction mixture was extracted with ethyl acetate. After the extract was dried over magnesium sulfate, ethyl acetate was distilled off, and the residue was purified by column chromatography on silica gel to obtain 4.48 g (yield: 56%) of the title compound as a colorless amorphous substance.

IR (KBr method, cm⁻¹): 3365, 1677, 1306, 1153, 1110.

¹H-NMR (CDCl₃, δ ppm): 7.98(4H,m), 7.56(3H,m), 7.24 (1H,dd,J=2.9 Hz), 3.90(2H,brs), 3.34(2H,s), 1.16(6H,s).

Example 2

Respective compounds (Compound Nos. 11–20) shown in Tables 4–6 were obtained in the same manner as in Example 1.

TABLE 4

| Compd. No. | Structural formula | mp (°C.) | IR(cm⁻¹) | NMR δ ppm(CDCl₃) |
|---|---|---|---|---|
| 11 | CF₃-[ring]-N(NH₂), C(=O), dimethyl | 74–76 | 1664 1338 | 7.98(1H, d, J=8Hz), 7.72(1H, s), 7.02(1H, d, J=8Hz), 3.84(2H, brs), 3.36(2H, s), 1.22(6H, s) |

TABLE 4-continued

| Compd. No. | Structural formula | mp (°C.) | IR(cm⁻¹) | NMR δ ppm(CDCl₃) |
|---|---|---|---|---|
| 12 | CF₃S-[structure with NH₂, N, O] | 64–65 | 3331 1684 | 7.91(1H, d, J=8Hz), 7.71(1H, d, J=2Hz), 7.04(1H, dd J=8.2Hz, 3.81(2H, brs), 3.34(2H, s), 1.20(6H, s) |
| 13 | Br-[structure with NH₂, N, O] | 87–88 | 1659 1590 | 7.74(1H, d, J=8Hz) 7.60(1H, d, J=2Hz), 6.94(1H, dd, J=8.2Hz), 3.78(2H, brs), 3.30(2H, s), 1.18(6H, s) |
| 14 | CF₃O-[structure with NH₂, N, O] | 50 . 51 | 3328 1674 1274 | 7.92(1H, d, J=8Hz), 7.26(1H, d, J=2Hz), 6.65(1H, dd, J=8.2Hz), 3.80(2H, brs), 3.34(2H, s), 1.20(6H, s) |

TABLE 5

| Compd. No. | Structural formula | mp (°C.) | IR(cm⁻¹) | NMR δ ppm(CDCl₃) |
|---|---|---|---|---|
| 15 | MeS-[structure with NH₂, N, O] | 85–86 | 3335 1654 1585 | 7.86(1H, d, J=8Hz), 7.25(1H, d, J=2Hz), 6.72(1H, dd, J=8.2Hz), 3.80(2H, s), 3.32(2H, s), 2.54(3H, s), 1.22(6H, s) |
| 16 | PhS-[structure with NH₂, N, O] | 83–84 | 1655 1578 | 7.80(1H, d, J=8Hz), 7.36–7.66(5H, m), 7.20(1H, d, J= 2Hz), 6.59(1H, dd, J=8.2Hz), 3.70(2H, s), 3.30(2H, s), 1.20(6H, s) |
| 17 | Cl, Cl-[structure with NH₂, N, O] | 107–110 | 3345 1664 1392 | 7.91(1H, s), 7.56(1H, s), 3.80(2H, brs), 3.30(2H, s), 1.17(6H, s) |
| 18 | NC-[structure with NH₂, N, O] | 112–114 | 2232 1670 1599 1394 | 7.92(1H, d, J=8.5Hz), 7.78(1H, d, J=1.5Hz), 7.02(1H, dd, J=8.5, 1.5Hz), 3.84(2H, brs), 3.37(2H, s), 1.21 (6H, s) |

TABLE 6

| Compd. No. | Structural formula | mp (°C.) | IR(cm⁻¹) | NMR δ ppm(CDCl₃) |
|---|---|---|---|---|
| 19 | PhSO₂—[structure with NH₂, N, O] | amorphous powder | 3365, 1677, 1306, 1153, 1110 | 7.98(4H, m), 7.56(3H, m), 7.24(1H, dd, J=2.9Hz), 3.90(2H, brs), 3.34(2H, s), 1.16(6H, s) |
| 20 | MeO—[structure with NH₂, N, O] | 110–112 | 1654, 1492, 1207, 1029 | 7.30–7.50(2H, m), 7.10(1H, dd, J=3.9Hz), 3.80(3H, s), 3.74(2H, brs), 3.22(2H, s), 1.20(6H, s) |

Example 3

1-Acetoamino-2,3-dihydro-3,3-dimethyl-7-phenylsulfonyl-4(1H)-quinolinone (Compound No. 53):

While stirring under chilling with ice water, 188 μl of acetic anhydride were added to a solution of 330 mg of 1-amino-2,3-dihydro-3,3-dimethyl-7-phenylsulfonyl-4(1H)-quinolinone in pyridine. After stirring overnight at room temperature, the liquid reaction mixture was extracted with chloroform with the system acidified with hydrochloric acid. After the extract was dried over magnesium sulfate, chloroform was distilled off, and the residue was purified by column chromatography on silica gel to obtain 287 mg (yield: 77%) of the title compound as yellow crystals.

m.p.: 162°–164° C. (hexane-diethyl ether).

IR (KBr method, cm⁻¹): 3222, 1687, 1603, 1157.

¹H-NMR (CDCl₃, δ ppm): 8.30(1H,s), 7.00–8.10(8H,m), 3.10–3.70(2H,m), 2.10(3H,s), 1.17, 1.22, 1.28(total 6H,s).

Example 4

2,3-Dihydro-3,3-dimethyl-7-phenylsulfonyl-1-(3-pyridinecarbamoyl)-4(1H)-quinolinone (Compound No. 55):

While stirring under chilling with ice water, 356 mg of nicotinic acid chloride hydrochloride were added to a solution of 330 mg of 1-amino-2,3-dihydro-3,3-dimethyl-7-phenylsulfonyl-4(1H)-quinolinone in pyridine. After stirring overnight at room temperature, the liquid reaction mixture was extracted with chloroform with the system basified with sodium hydroxide. After the extract was dried over magnesium sulfate, chloroform was distilled off, and the residue was purified by column chromatography on silica gel to obtain 354 mg (yield: 81%) of the title compound as a colorless amorphous substance.

IR (KBr method, cm⁻¹): 1686, 1603, 1306, 1285, 1155.

¹H-NMR (CDCl₃, δ ppm): 9.71(1H,s), 9.17(1H,d,J=2 Hz), 8.78(1H,dd,J=2.5 Hz), 8.26(1H,dt,J=8.2 Hz), 7.94(1H, d,J=9 Hz), 7.84(2H,m), 7.49(5H,m), 7.16(1H,dd,J=2.9 Hz), 3.65(2H,s), 1.22(6H,s).

Example 5

2,3-Dihydro-3,3-dimethyl-7-phenylsulfonyl-1-(2-oxopyrrolidin-1-yl)-4(1H)-quinolinone (Compound No. 63):

While stirring under chilling with ice water, 220 μl of chlorobutyryl chloride were added to a solution of 550 mg of 1-amino-2,3-dihydro-3,3-dimethyl-7-phenylsulfonyl-4 (1H)-quinolinone in pyridine. After stirring overnight at room temperature, the liquid reaction mixture was extracted with chloroform with the system acidified with hydrochloric acid. After the extract was dried over magnesium sulfate, chloroform was distilled off. The residue was dissolved in dimethylformamide, and 91 mg of sodium hydride were added to the solution under chilling with ice water to stir the resultant mixture at room temperature for 30 minutes. After completion of the reaction, ice water was added to the liquid reaction mixture, which was then extracted with diethyl ether. After the extract was dried over magnesium sulfate, diethyl ether was distilled off, and the residue was purified by column chromatography on silica gel to obtain 249 mg (yield: 41%) of the title compound as yellow crystals.

m.p.: 197°–199° C. (hexane-diethyl ether).

IR (KBr method, cm⁻¹): 1714, 1682, 1158.

¹H-NMR (CDCl₃, δ ppm): 7.90(3H,m), 7.58(3H,m), 7.30 (2H,m), 3.76(1H,d,J=11 Hz), 3.62(2H,m), 3.26(1H,d,J=11 Hz), 2.00–2.70(2H,m), 1.24(3H,s), 1.19(3H,s).

Example 6

2,3-Dihydro-3,3-dimethyl-7-phenylsulfonyl-1-(N-propanoyl-N-methylamino)-4(1H)-quinolinone (Compound No. 62):

While stirring under chilling with ice water, 13 mg of sodium hydride were added to a solution of 120 mg of 2,3-dihydro-3,3-dimethyl-7-phenylsulfonyl-1-propanoyl-amino-4(1H)-quinolinone in dimethylformamide, and the mixture was stirred at room temperature for 15 minutes. The mixture was chilled again with ice water and added with 20 μl of methyl iodide, and the resultant mixture was stirred at room temperature for 30 minutes. After completion of the reaction, ice water was added to the liquid reaction mixture, which was then extracted with diethyl ether. After the extract was dried over magnesium sulfate, diethyl ether was distilled off, and the residue was purified by column chromatography on silica gel to obtain 106 mg (yield: 85%) of the title compound as yellow crystals.

m.p.: 153°–155° C. (hexane-diethyl ether).

IR (KBr method, cm⁻¹): 1676, 1310, 1154.

¹H-NMR (CDCl₃, δ ppm): 7.80–8.20(3H,m) , 7.40–4.80 (4H,m), 7.15–7.30(1H,m), 3.68(1H,½ABq,J=13 Hz), 3.14

(1H,½ABq,J=13 Hz), 3.01(3H,s), 2.44(2H,q,J=7 Hz), 1.28 (3H,s), 1.26(3H,s), 1.13(3H,t,J=7 Hz).

Example 7

2,3-Dihydro-3,3-dimethyl-7-methylsulfinyl-1-(3-pyridinecarbamoyl)-4(1H)-quinolinone (Compound No. 41):

An aqueous solution of 95 mg of sodium periodate was added to a solution of 126 mg of 2,3-dihydro-3,3-dimethyl-7-methylthio-1-(3-pyridinecarbamoyl)-4(1H)-quinolinone in methanol, and the mixture was stirred for 24 hours. The liquid reaction mixture was added with saturated saline and extracted with ethyl acetate. After the extract was dried over magnesium sulfate, ethyl acetate was distilled off, and the residue was purified by column chromatography on silica gel to obtain 97 mg (yield: 73%) of the title compound as a colorless amorphous substance.

IR (KBr method, cm$^{-1}$): 1684, 1599, 1284, 1027.

$^1$H-NMR (CDCl$_3$, δ ppm): 10.58(1H,s), 9.22(1H,m), 8.75 (1H,m), 8.30(1H,m), 8.02(1H,d,J=8 Hz), 7.24–7.50(2H,m), 6.82(1H,dd,J=8,2 Hz), 3.70(2H,m), 2.68(3H,s), 1.32(3H,s), 1.29(3H,s).

Example 8

1-Acetoamino-2,3-dihydro-3,3-dimethyl-7-(trifluoromethyl) sulfonyl-4(1H)-quinolinone (Compound No. 44):

After 208 mg of m-chloroperbenzoic acid were added to a solution of 160 mg of 1-acetoamino-2,3-dihydro-3,3-dimethyl-7-(trifluoromethyl)sulfinyl-4(1H)-quinolinone in methylene chloride, and the mixture was stirred at room temperature for 30 minutes, it was held under reflux for 8 hours. After 104 mg of m-chloroperbenzoic acid were additionally added, and the resultant mixture was held under reflux for 4 hours, the liquid reaction mixture was diluted with methylene chloride. Thereafter, the dilute reaction mixture was washed successively with a saturated aqueous solution of sodium sulfite and saturated saline and then dried over magnesium sulfate. Methylene chloride was then distilled off, and the residue was purified by column chromatography on silica gel to obtain 29 mg (yield: 17%) of the title compound as colorless crystals.

m.p.: 166°–167° C. (hexane-diethyl ether).

IR (KBr method, cm$^{-1}$): 1700, 1366, 1219, 1133.

$^1$H-NMR (CDCl$_3$, δ ppm): 7.09–8.30(4H,m), 3.38–3.90 (2H,m), 2.14–2.17(3H,m), 1.22–1.40(6H,m).

Example 9

Respective compounds (Compound Nos. 21–72) shown in Tables 7–20 were obtained in the same manner as in Examples 1–8.

TABLE 7

| Compd. No. | Structural formula | mp (°C.) | IR(cm$^{-1}$) | NMR δ ppm(CDCl$_3$) |
|---|---|---|---|---|
| 21 | CF$_3$—(ring)—N(NHCOMe)—...—O | 182–183 | 1686 | 7.00–8.20(4H, m), 3.20–3.65(2H, m), 2.12–2.16(3H, m), 1.20–1.30(6H, m) |
| 22 | CF$_3$—(ring)—N(NHCOEt)—...—O | 139–141 | 1655 | 7.00–8.20(4H, m), 3.20–3.65(2H, m), 2.15–2.62(2H, m), 1.00–1.40(9H, m) |
| 23 | CF$_3$—(ring)—N(NHCO-pyridyl)—...—O | 190–192 | 3215, 1686 | 9.16(2H, m), 8.77(1H, m), 7.92–8.34(2H, m), 7.00–7.60(3H, m), 3.66(2H, s), 1.26(6H, s) |
| 24 | Br—(ring)—N(NHCOMe)—...—O | 198–200 | 3220, 1676, 1595 | 6.82–7.90(4H, m), 3.14–3.62(2H, m), 2.10–2.16(3H, m), 1.10–1.40(6H, m) |

TABLE 8

| Compd. No. | Structural formula | mp (°C.) | IR(cm⁻¹) | NMR δ ppm(CDCl₃) |
|---|---|---|---|---|
| 25 | Br-[quinolinone with NHCOEt] | 169–170 | 3261, 1685, 1665, 1595 | 6.92–7.90(4H, m), 3.12–3.60(2H, m), 2.18–2.60(2H, m), 1.10–1.40(9H, m) |
| 26 | Br-[quinolinone with NHCO-pyridyl] | 202–203 | 1684, 1594 | 9.14(1H, m), 8.99(1H, s), 8.81(1H, m), 8.26(1H, m), 7.78(1H, d, J=8Hz), 7.38(1H, m), 7.04(2H, m), 3.62 (2H, s), 1.24(6H, s) |
| 27 | Br-[quinolinone with NHCO-C₆H₄-NO₂] | 100–103 | 1685, 1594 | 9.26(1H, s), 8.74(1H, m), 8.36(2H, m), 7.70(2H, m), 6.96(2H, m), 3.60(2H, s), 1.19(6H, s) |
| 28 | CF₃O-[quinolinone with NHCOMe] | 126–127 | 3244, 1684, 1617, 1252 | 7.48–8.10(2H, m), 6.58–6.94(2H, m), 2.18–2.62(2H, m), 2.08–2.14(3H, m), 1.12–1.40(6H, m) |

TABLE 9

| Compd. No. | Structural formula | mp (°C.) | IR(cm⁻¹) | NMR δ ppm(CDCl₃) |
|---|---|---|---|---|
| 29 | CF₃O-[quinolinone with NHCOEt] | 91–92 | 3196, 1671, 1617, 1278 | 7.68–8.10(2H, m), 6.56–6.90(2H, m), 3.18–3.60(2H, m), 2.14–2.50(2H, m), 1.00–1.38(9H, m) |
| 30 | CF₃O-[quinolinone with NHCO-pyridyl] | 145–146 | 1685, 1618, 1257 | 8.70–9.20(3H, m), 7.88–8.32(2H, m), 7.36–7.60(1H, m), 6.60–6.90(2H, m), 3.66(2H, s), 1.24(6H, s) |

TABLE 9-continued

| Compd. No. | Structural formula | mp (°C.) | IR(cm⁻¹) | NMR δ ppm(CDCl₃) |
|---|---|---|---|---|
| 31 | CF₃O-[quinolinone with NHCO-C₆H₄-Cl substituent on N] | 142–143 | 3241<br>1685<br>1664<br>1258 | 8.52(1H, s), 7.30–8.06(5H, m), 6.60–6.82(2H, m), 3.62(2H, s), 1.21(6H, s) |
| 32 | CF₃O-[quinolinone with NHCO-C(CH₃)₂-CH₂Cl on N] | 162–163 | 3242<br>1684<br>1616<br>1271 | 7.96(1H, d, J=8Hz), 7.96(1H, s), 6.60–6.80(2H, m), 3.64(2H, s), 3.53(2H, s), 1.40(6H, s), 1.20(6H, s) |

TABLE 10

| Compd. No. | Structural formula | mp (°C.) | IR(cm⁻¹) | NMR δ ppm(CDCl₃) |
|---|---|---|---|---|
| 33 | CF₃O-[quinolinone with N-azetidinone] | 76–77 | 1762<br>1682<br>1616<br>1264 | 8.00(1H, d, J=8Hz), 6.60–6.88(2H, m), 3.46(2H, s), 3.40(2H, s), 1.44(6H, s), 1.25(6H, s) |
| 34 | MeS-[quinolinone with NHCOMe on N] | 137–138 | 3226<br>1665<br>1595 | 7.20–7.92(2H, m), 6.60–6.96(2H, m), 3.15–3.60(2H, m), 2.48–2.51(3H, m), 2.14–2.20(3H, m), 1.15–1.40 (6H, m) |
| 35 | MeS-[quinolinone with NHCOEt on N] | 121–122 | 3287<br>1673<br>1593 | 7.05–7.92(2H, m), 6.60–6.96(2H, m), 3.10–3.60(2H, m), 2.20–2.66(5H, m), 1.06–1.24(9H, m) |
| 36 | MeS-[quinolinone with NHCO-pyridyl on N] | amorphous powder | 1670<br>1593 | 9.18(1H, m), 8.70–9.00(2H, m), 8.30(1H, m), 7.88 (1H, d, J=8Hz), 7.50(1H, m), 6.68–6.86(2H, m), 3.62 (2H, s), 2.42(3H, s), 1.25(6H, s) |

TABLE 11

| Compd. No. | Structural formula | mp (°C.) | IR(cm⁻¹) | NMR δ ppm(CDCl₃) |
|---|---|---|---|---|
| 37 | PhS-[Ar]-N(NHCOMe)-[ring]-C(=O) | 201–202 | 1670, 1593 | 7.30–7.92(7H, m), 6.44–6.80(2H, m), 3.15–3.60(2H, m), 1.93–2.11(3H, m), 1.16–1.40(6H, m) |
| 38 | PhS-[Ar]-N(NHCOEt)-[ring]-C(=O) | 159–160 | 1674, 1593 | 7.30–7.84(7H, m), 6.42–6.82(2H, m), 3.12–3.60(2H, m), 2.00–2.62(2H, m), 1.00–1.35(9H, m) |
| 39 | PhS-[Ar]-N(NHCO-3-pyridyl)-[ring]-C(=O) | 183–184 | 1663, 1593 | 8.78–8.94(2H, m), 8.51(1H, s), 8.10(1H, m), 7.82 (1H, d, J=8Hz), 7.18–7.62(6H, m), 6.70(1H, dd, J=8, 2Hz), 6.48(1H, d, J=2Hz), 3.60(2H, s), 1.23(6H, s) |
| 40 | MeSO₂-[Ar]-N(NHCOMe)-[ring]-C(=O) | 169–170 | 1681, 1605, 1296, 1150 | 7.75–8.25(2H, m), 7.18–7.60(2H, m), 3.20–3.75(2H, m), 3.02–3.06(3H, m), 2.10–2.16(3H, m), 1.12–1.40 (6H,m) |

TABLE 12

| Compd. No. | Structural formula | mp (°C.) | IR(cm⁻¹) | NMR δ ppm(CDCl₃) |
|---|---|---|---|---|
| 41 | MeSO-[Ar]-N(NHCO-3-pyridyl)-[ring]-C(=O) | amorphous powder | 1684, 1599, 1284, 1027 | 10.58(1H, s), 9.22(1H, m), 8.75(1H, m), 8.30(1H, m), 8.02(1H, d, J=8Hz), 7.24–7.50(2H, m), 6.82(1H, dd, J=8.2Hz), 3.70(2H, m), 2.68(3H, s), 1.32(3H, s), 1.29(3H, s) |
| 42 | PhSO-[Ar]-N(NHCOMe)-[ring]-C(=O) | amorphous powder | 1684, 1599 | 9.07(1H, s), 7.92(1H, d, J=8Hz), 7.20–7.70(6H, m), 6.74(1H, dd, J=8, 2Hz), 3.50(2H, m), 2.15(3H, s), 1.05–1.20(6H, m) |
| 43 | CF₃S-[Ar]-N(NHCOMe)-[ring]-C(=O) | 99–101 | 1685, 1598 | 7.60–8.10(2H, m), 7.04–7.40(2H, m), 3.20–3.66(2H, m), 2.06–2.20(3H, m), 1.15–1.40(6H, m) |

TABLE 12-continued

| Compd. No. | Structural formula | mp (°C.) | IR(cm⁻¹) | NMR δ ppm(CDCl₃) |
|---|---|---|---|---|
| 44 | CF₃SO₂-[structure with NHCOMe] | 166–167 | 1700, 1366, 1219, 1133 | 7.09–8.30(4H, m), 3.38–3.90(2H, m), 2.14–2.17(3H, m), 1.22–1.40(6H, m) |

TABLE 13

| Compd. No. | Structural formula | mp (°C.) | IR(cm⁻¹) | NMR δ ppm (CDCl₃) |
|---|---|---|---|---|
| 45 | Cl,Cl-[structure with NHCOMe] | 158–160 | 2969, 1676, 1597 | 8.03, 7.96(total 1H, s), 7.81, 7.43(total 1H, brs), 7.13, 6.94(total 1H, s), 2.10–2.70(total 2H, m), 2.16, 2.10(total 3H, s), 1.30, 1.24, 1.20(total 6H, s) |
| 46 | Cl,Cl-[structure with NHCOEt] | 176–178 | 3231, 1670, 1600 | 8.00, 7.94, 7.32, 7.10, 6.90(total 3H, s), 3.10–3.70 (total 2H, m), 2.00–2.60(total 2H, m), 1.00–1.40 (total 9H, m) |
| 47 | Cl,Cl-[structure with NHCO-pyridyl] | 241–243 | 3448, 1676, 1602 | 9.12(1H, d, J=2Hz), 8.77(1H, dd, J=5, 2Hz), 8.34(1H, dt, J=8, 2Hz), 7.99(1H, s), 7.52(1H, dd, J=8, 5Hz), 7.01(1H, s), 3.64(2H, brs), 1.46(6H, s) |
| 48 | Cl,Cl-[structure with NHCO-phenyl-NO₂] | 200–202 | 3196, 1686, 1537, 1356 | 8.83(1H, t, J=2Hz), 8.30–8.57(3H, m), 7.97(1H, s), 1.74(1H, t, J=9Hz), 7.00(1H, s), 3.62(2H, brs), 1.26 (6H, s) |

TABLE 14

| Compd. No. | Structural formula | mp (°C.) | IR(cm⁻¹) | NMR δ ppm (CDCl₃) |
|---|---|---|---|---|
| 49 | (6,7-dichloro quinolinone with NHCO-furan substituent) | 203–205 | 3303, 1691, 1671, 1154 | 7.97(1H, s), 7.60(1H, dd, J=2, 1Hz), 7.28(1H, dd, J=4, 1Hz), 7.06(1H, s), 6.60(1H, dd, J=4, 2Hz), 3.59(2H, brs), 1.24(6H, s) (CDCl₃ + CD₃OD) |
| 50 | (NC-substituted quinolinone with NHCOMe) | 164–165 | 2232, 1680, 1610, 1435, 1279 | 7.60–8.20(2H, m), 7.00–7.40(2H, m), 3.20–3.70(2H, m), 2.00–2.25(3H, m), 1.00–1.45(6H, m) |
| 51 | (NC-substituted quinolinone with NHCOEt) | 178–180 | 2227, 1681, 1558 | 7.70–8.10(2H, m), 7.00–7.20(2H, m), 3.60(2H, m), 2.20–2.50(2H, m), 1.00–1.45(9H, m) |
| 52 | (NC-substituted quinolinone with NHCO-pyridyl) | 197–199 | 2233, 1696, 1664, 1609, 1290 | 9.24(1H, brs), 9.16(1H, d, J=2Hz), 8.84(1H, dd, J=5, 2Hz), 8.28(1H, dt, J=8, 2Hz), 8.02(1H, d, J=8Hz), 7.52(1H, dd, J=8, 5Hz), 7.00–7.30(2H, m), 3.72(2H, brs), 1.26(6H, s) |

TABLE 15

| Compd. No. | Structural formula | mp (°C.) | IR(cm⁻¹) | NMR δ ppm (CDCl₃) |
|---|---|---|---|---|
| 53 | (PhSO₂-substituted quinolinone with NHCOMe) | 162–164 | 3222, 1687, 1603, 1157 | 8.30(1H, s), 7.00–8.10(8H, m), 3.10–3.70(2H, m), 2.10(3H, s), 1.17, 1.22, 1.28(total 6H, s) |
| 54 | (PhSO₂-substituted quinolinone with NHCOEt) | 145–146 | 3267, 1684, 1308, 1155 | 8.28(1H, s), 7.06–8.08(8H, m), 3.10–3.80(2H, m), 2.32(2H, q, J=7Hz), 1.00–1.40(6H, m) |

TABLE 15-continued

| Compd. No. | Structural formula | mp (°C.) | IR(cm⁻¹) | NMR δ ppm (CDCl₃) |
|---|---|---|---|---|
| 55 | (PhSO₂-substituted dihydroquinolinone with NHCO-pyridin-3-yl) | amorphous powder | 1686, 1603, 1306, 1285, 1155 | 9.71(1H, s), 9.17(1H, d, J=2Hz), 8.78(1H, dd, J=2, 5 Hz), 8.26(1H, dt, J=8, 2Hz), 7.94(1H, d, J=9Hz), 7.84 (2H, m), 7.49(5H, m), 7.16(1H, dd, J=2, 9Hz), 3.65 (2H, s), 1.22(6H, s) |
| 56 | (PhSO₂-substituted dihydroquinolinone with NHCO-CH₂CH(CH₃)₂) | 147–149 | 3227, 1693, 1665, 1602, 1157 | 7.10–8.30(9H, m), 3.54(2H, brs), 2.18(3H, m), 1.19 (6H, s), 1.04(6H, m) |

TABLE 16

| Compd. No. | Structural formula | mp (°C.) | IR(cm⁻¹) | NMR δ ppm (CDCl₃) |
|---|---|---|---|---|
| 57 | (PhSO₂-substituted dihydroquinolinone with NHCO-phenyl) | 248–250 | 3254, 1693, 1665, 1154 | 7.10–8.10(14H, m), 3.63(2H, brs), 1.25(6H, s), (CDCl₃ + CD₃OD) |
| 58 | (PhSO₂-substituted dihydroquinolinone with NHCO-C₆H₄-Me) | 264–266 | 1690, 1664, 1153 | 8.02(2H, d, J=9Hz), 7.10–8.00(1H, m), 3.62(2H, brs), 2.45(3H, s), 1.24(6H, s) (CDCl₃ + CD₃OD) |
| 59 | (PhSO₂-substituted dihydroquinolinone with NHCO-cyclohexyl) | 175–177 | 3251, 1693, 1676, 1157 | 7.10–8.20(9H, m), 3.52(2H, brs), 1.16(6H, s), 1.00–2.40(11H, m) |
| 60 | (PhSO₂-substituted dihydroquinolinone with NHCO-2,4-difluorophenyl) | 212–213 | 1697, 1616, 1275, 1155 | 6.80–8.80(12H, m), 3.65(2H, brs), 1.23(6H, s) |

TABLE 17

| Compd. No. | Structural formula | mp (°C.) | IR(cm⁻¹) | NMR δ ppm (CDCl₃) |
|---|---|---|---|---|
| 61 | PhSO₂-[quinolinone with NHCO-furan substituent] | 205–207 | 1691, 1669, 1448, 1315, 1156 | 8.58(1H, brs), 7.90(3H, m), 7.55(5H, m), 7.25(2H, m), 6.60(1H, dd, J=2, 4Hz), 3.62(2H, brs), 1.22(6H, s) |
| 62 | PhSO₂-[quinolinone with Me—N—COEt substituent] | 153–155 | 1676, 1310, 1154 | 7.80–8.20(3H, m), 7.40–7.80(4H, m), 7.15–7.30(1H, m), 3.68(1H, 1/2ABq, J=13Hz), 3.14(1H, 1/2ABq, J=13 Hz), 3.01(3H, s), 2.44(2H, q, J=7Hz), 1.28(3H, s), 1.26(3H, s), 1.13(3H, t, J=7Hz) |
| 63 | PhSO₂-[quinolinone with pyrrolidinone substituent] | 197–199 | 1714, 1682, 1158 | 7.90(3H, m), 7.58(3H, m), 7.30(2H, m), 3.76(1H, d, J=11Hz), 3.62(2H, m), 3.26(1H, d, J=11Hz), 2.00–2.70(2H, m), 1.24(3H, s), 1.19(3H, s) |
| 64 | MeO-[quinolinone with NHCOMe substituent] | 149–151 | 1676, 1492, 1281, 1031 | 6.70–7.70(4H, m), 3.82, 3.78(total 3H, s), 3.48, 3.40, 3.20(total 2H, brs, d, d, J=11Hz), 2.16, 2.09 (total 3H, s), 1.31, 1.25, 1.22(total 6H, s) |

TABLE 18

| Compd. No. | Structural formula | mp (°C.) | IR(cm⁻¹) | NMR δ ppm (CDCl₃) |
|---|---|---|---|---|
| 65 | MeO-[quinolinone with NHCOEt substituent] | 175–177 | 1677, 1493, 1030 | 6.70–7.70(4H, m), 3.82, 3.78(total 3H, s), 3.48, 3.40, 3.20(total 2H, brs, d, d, J=11Hz), 2.10–2.70 (total 2H, m), 1.00–1.40(total 9H, m) |
| 66 | MeO-[quinolinone with NHCO-pyridyl substituent] | 164–166 | 1676, 1654, 1492 | 9.14(1H, d, J=2Hz), 8.80(2H, m), 8.25(1H, dt, J=7, 2 Hz), 6.70–7.60(4H, m), 3.78(3H, s), 3.58(2H, s), 1.26(6H, s) |

TABLE 18-continued

| Compd. No. | Structural formula | mp (°C.) | IR(cm⁻¹) | NMR δ ppm (CDCl₃) |
|---|---|---|---|---|
| 67 | (7-Br, 3,3-dimethyl-4-oxo-1,2,3,4-tetrahydroquinolin-1-yl pyrrolidin-2-one) | 186–188 | 1709 1675 1591 1480 | 7.80(1H, d, J=9Hz), 7.02(1H, dd, J=9, 2Hz), 6.83(1H, d, J=2Hz), 3.78(1H, 1/2ABq, J=12Hz), 3.62(2H, t, J=7Hz), 3.21(1H, 1/2ABq, J=12Hz), 2.00–2.70(4H, m), 1.27(3H, s), 1.20(3H, s) |

TABLE 19

| Compd. No. | Structural formula | mp (°C.) | IR(cm⁻¹) | NMR δ ppm (CDCl₃) |
|---|---|---|---|---|
| 68 | (7-F₃CO, 3,3-dimethyl-4-oxo-1,2,3,4-tetrahydroquinolin-1-yl pyrrolidin-2-one) | 91–93 | 1708 1674 1614 1248 1210 1169 | 8.00(1H, d, J=9Hz), 6.60–6.88(1H, m), 6.46(1H, m), 3.80(1H, 1/2ABq, J=13Hz), 3.62(2H, t, J=7Hz), 3.26(1H, 1/2ABq, J=13Hz), 2.00–2.70(4H, m), 1.28(3H, s), 1.22(3H, s) |
| 69 | (7-Br, 3,3-dimethyl-4-oxo-1,2,3,4-tetrahydroquinolin-1-yl piperidin-2-one) | 171–173 | 1679 1659 1476 1158 | 7.79(1H, d, J=9Hz), 6.96(1H, dd, J=9, 2Hz), 6.72(1H, d, J=2Hz), 4.00(1H, 1/2ABq, J=13Hz), 3.62(2H, t, J=6Hz), 3.10(1H, 1/2ABq, J=13Hz), 2.55(2H, t, J=6Hz), 1.50–2.30(4H, m), 1.17(3H, s), 1.15(3H, s) |
| 70 | (7-PhSO₂, 3,3-dimethyl-4-oxo-1,2,3,4-tetrahydroquinolin-1-yl piperidin-2-one) | 182–184 | 1681 1669 1299 1158 | 7.80–8.20(3H, m), 7.40–7.70(3H, m), 7.10–7.40(2H, m), 3.98(1H, 1/2ABq, J=13Hz), 3.64(2H, t, J=6Hz), 3.18(1H, 1/2ABq, J=13Hz), 2.54(2H, t, J=6Hz), 1.60–2.30(4H, m), 1.22(3H, s), 1.19(3H, s) |

TABLE 20

| Compd. No. | Structural formula | mp (°C.) | IR(cm⁻¹) | NMR δ ppm |
|---|---|---|---|---|
| 71 | CF₃SO₂—[quinolinone with NHCOC₂H₅] | 199–200 | 1701, 1669, 1217 | (CDCl₃) 8.17(1H, d, J=8Hz), 7.78(1H, s), 7.30–7.55(2H, m), 3.64(2H, m), 2.34(2H, q, J=7Hz), 1.05–1.24(9H, m) |
| 72 | CF₃SO₂—[quinolinone with NHCO-pyridyl] | 217–219 | 1693, 1361, 1215 | (CDCl₃—CD₃OD) 9.10(1H, m), 8.76(1H, m), 8.12–8.40(2H, m), 7.40–7.64(3H, m), 3.74(2H, br), 1.31(6H, s) |

Test Example 1

(Effect of inhibiting contraction caused by 30 mM K on endothelium-ablated specimen of rat thoracic aorta)

A thoracic aorta was enucleated from a rat (weight: 129–492 g) and cut into lengths of 3 mm. Cotton in the form of a paper string was put in a lumen of each of ring specimens, and the inner surface of the ring specimen was rubbed several times with the cotton, thereby ablating an endothelium from the thoracic aorta specimen. This specimen was incubated at 37° C. and suspended in 10 ml of a Krebs-Henseleit solution, into which a mixed gas had been introduced, with a load of 2 g applied thereto. The tension thereof was isometrically recorded in a recorder through an FD transducer and a dynamic strain gage. After at least 60 minutes went on after the suspension, and the sample was stabilized, $10^{-7}$M noradrenaline was applied several times to the specimen. Under contraction caused by $10^{-7}$M noradrenaline, $10^{-7}$M acetylcholine was applied to the specimen. A specimen which manifested no relaxing effect at this time was used in an experiment as an endothelium-ablated specimen. Each of agents (compounds of Compound Numbers shown in Table 20 and Cromakalim) to be tested was cumulatively applied at intervals of 10 minutes from the time 30 mM K⁺ had been applied to such a specimen, and the contraction of the specimen had been fixed, thereby calculating a median inhibitory concentration ($IC_{50}$). Incidentally, $10^{-4}$M papaverine was applied to confirm 100% relaxing affect. The agents to be tested were dissolved ($5 \times 10^{-2}$M in dimethyl sulfoxide and diluted with purified water before their use.

As a result, the compounds according to the present invention exhibited an effect of inhibiting the contraction of a smooth muscle on the basis of an excellent potassium channel-activating effect as shown in Table 20.

TABLE 20

| Compound No. | $IC_{50}$ (× $10^{-8}$ M) |
|---|---|
| 21 | 10.0 |
| 23 | 6.62 |
| 28 | 4.82 |
| 29 | 10.4 |
| 30 | 4.92 |
| 44 | 1.88 |

TABLE 20-continued

| Compound No. | $IC_{50}$ (× $10^{-8}$ M) |
|---|---|
| 53 | 8.32 |
| 63 | 8.69 |
| Cromakalim | 13.0 |

Preparation Example 1

(Tablet preparation)

Two grams of a 4-quinolinone derivative (1) or a salt thereof 130 g mannite, 40 g of potato starch and 8 g of magnesium stearate were used. They were mixed and tableted in a method per se in the art, thereby obtaining a tablet preparation of 1,000 tablets in total, which each had a weight of 180 mg.

Preparation Example 2

(Injection preparation)

One gram of a 4-quinolinone derivative (1) or a salt thereof, which had been sterilized, was first dissolved in distilled water for injection so as to give a total volume of 1 liter. The solution was then sterilely, hermetically charged into ampules in a proportion of 5 ml/ample, thereby obtaining an injection preparation.

INDUSTRIAL APPLICABILITY

The 4-quinolinone derivative (1) or the salt thereof according to the present invention has an excellent potassium channel-activating effect and is useful as, for example, a prophylactic and therapeutic agent for diseases of circulatory and bronchial systems.

We claims:

1. A 4-quinolinone derivative represented by the following general formula (1):

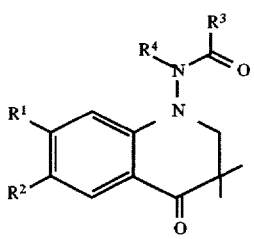

(1)

wherein $R^1$ and $R^2$ may be the same or different from each other and mean individually a hydrogen atom; a halogen atom; a cyano group; a lower alkyl, lower alkylsulfonyl, lower alkylsulfinyl, lower alkylthio or lower alkoxy group which may be substituted by halogen atom; or a phenylsulfonyl, phenylsulfinyl or phenylthio group which may have a substituent; and $R^3$ and $R^4$ may be the same or different from each other and denote individually a hydrogen atom; a lower alkyl or cycloalkyl group which may be substituted by halogen atom; or a pyridyl, furanyl or phenyl group which may have a substituent, or $R^3$ and $R^4$ may form a 4-, 5- or 6-membered heterocyclic ring, which may be substituted by a lower alkyl group, together with the adjacent carbon atom and nitrogen atom, or a salt thereof.

2. The 4-quinolinone derivative or the salt thereof according to claim 1, wherein $R^1$ and $R^2$ may be the same or different from each other and mean individually a hydrogen atom; a halogen atom; a cyano group; an alkyl, alkylsulfonyl, alkylsulfinyl, alkylthio or alkoxy group which has 1–6 carbon atoms and may be substituted by 1–3 halogen atoms; a phenylsulfonyl group; a phenylsulfinyl group; or a phenylthio group; and $R^3$ and $R^4$ may be the same or different from each other and denote individually a hydrogen atom; an alkyl group having 1–6 carbon atoms or a cycloalkyl group having 3–6 carbon atoms, which may be substituted by 1–3 halogen atoms; or a pyridyl, furanyl or phenyl group which may be substituted by a substituent selected from a halogen atom, a hydroxyl group, an alkoxy group having 1–6 carbon atoms, an aryloxy group, an aralkyloxy group, a nitroxy group, an amino group, a cyano group, a nitro group, an alkylamino group having 1–6 carbon atoms, a dialkylamino group having 2–12 carbon atoms, a cyclic amino group, an aryl group, an aminosulfonyl group or an alkyl group having 1–6 carbon atoms, or $R^3$ and $R^4$ may form a 2-oxoazetidinyl, 2-oxopyrrolidinyl or 2-oxopiperidinyl group, which may be substituted by an alkyl group having 1–6 carbon atoms, together with the adjacent carbon atom and nitrogen atom.

3. An N-amino-4-quinolinone derivative represented by the following general formula (2):

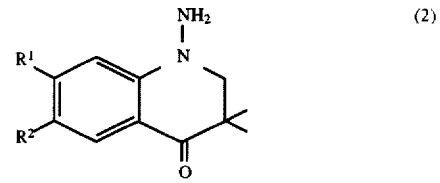

(2)

wherein $R^1$ and $R^2$ may be the same or different from each other and mean individually a hydrogen atom; a halogen atom; a cyano group; a lower alkyl, lower alkylsulfonyl, lower alkylsulfinyl, lower alkylthio or lower alkoxy group which may be substituted by halogen atom; or a phenylsulfonyl, phenylsulfinyl or phenylthio group which may have a substituent, or a salt thereof.

4. The N-amino-4-quinolinone derivative or the salt thereof according to claim 3, wherein $R^1$ and $R^2$ may be the same or different from each other and mean individually a hydrogen atom; a halogen atom; a cyano group; an alkyl, alkylsulfonyl, alkylsulfinyl, alkylthio or alkoxy group which has 1–6 carbon atoms and may be substituted by 1–3 halogen atoms; a phenylsulfonyl group; a phenylsulfinyl group; or a phenylthio group.

5. A medicinal composition comprising the 4-quinolinone derivative or the salt thereof according to claim 1 and a pharmaceutically acceptable carrier for medicines.

6. The medicinal composition according to claim 5, which is suitable for use in treating a disease of circulatory or bronchial system.

7. The medicinal composition according to claim 5, which is suitable for use in treating an ischemic heart disease, hypertension or bronchial asthma.

8. A method of treating a disease of the circulatory or bronchial system, comprising administering to a patient in need thereof an effective amount of the 4-quinolinone derivative or salt thereof according to claim 1.

9. The method of claim 8, wherein said disease is ischemic heart disease, hypertension or bronchial asthma.

* * * * *